(12) United States Patent
Kitano

(10) Patent No.: US 9,380,988 B2
(45) Date of Patent: Jul. 5, 2016

(54) ELECTRONIC CASSETTE FOR RADIOGRAPHIC IMAGING

(71) Applicant: FUJIFILM Corporation, Tokyo (JP)

(72) Inventor: Kouichi Kitano, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 152 days.

(21) Appl. No.: 14/168,413

(22) Filed: Jan. 30, 2014

(65) Prior Publication Data

US 2014/0226795 A1    Aug. 14, 2014

(30) Foreign Application Priority Data

Feb. 12, 2013   (JP) .................................. 2013-024048
Jan. 21, 2014   (JP) .................................. 2014-008504

(51) Int. Cl.
*A61B 6/00*    (2006.01)
*A61B 6/10*    (2006.01)

(52) U.S. Cl.
CPC ............. *A61B 6/4283* (2013.01); *A61B 6/4488* (2013.01); *A61B 6/56* (2013.01); *A61B 6/107* (2013.01); *A61B 6/4405* (2013.01)

(58) Field of Classification Search
CPC ...... A61B 6/4283; A61B 6/4488; A61B 6/56; H02J 7/025
USPC ....................................................... 320/108
See application file for complete search history.

(56) References Cited

U.S. PATENT DOCUMENTS 7,866,163 B2    1/2011  Ertel
8,907,752 B2 *  12/2014 Wodrich ............... G06F 1/1635
                                        335/205
2010/0253153 A1* 10/2010 Kondo ................. H01F 27/2876
                                        307/104
2013/0301803 A1* 11/2013 Liu ......................... A61B 6/42
                                        378/114

FOREIGN PATENT DOCUMENTS

JP    2004-252562 A    9/2004
JP    2006-102492 A    4/2006
JP    2012-239657 A    12/2012

OTHER PUBLICATIONS

Chinese Office Action, dated May 28, 2014, for Chinese Application No. 201420057634.6, including a English translation.
Japanese Office Action, dated Feb. 24, 2016, for counterpart Japanese Application No. 2014-008504, with an English translation.

* cited by examiner

*Primary Examiner* — Robert Kim
*Assistant Examiner* — Eliza Osenbaugh-Stewar
(74) *Attorney, Agent, or Firm* — Birch, Stewart, Kolasch & Birch, LLP

(57) ABSTRACT

An electronic cassette for radiographic imaging includes a radiation imaging detector for detecting X-rays from an object and creating an X-ray image of the object. A battery supplies the radiation imaging detector with power. A power receiver wirelessly receives power from a wireless power transmission apparatus for charging the battery. A housing is formed from an electrical conductor, for containing the radiation imaging detector and the power receiver. A path opening is formed in the housing, and disposed between the power receiver and the wireless power transmission apparatus. A cover device is formed from a material having electrical insulating property and thermal conductivity, for closing the path opening, and conducting heat of the power receiver to the housing for dissipation. Preferably, the cover device contains synthetic resin. Also, a profile line of the path opening is at least partially curved.

18 Claims, 12 Drawing Sheets

F I G . 15
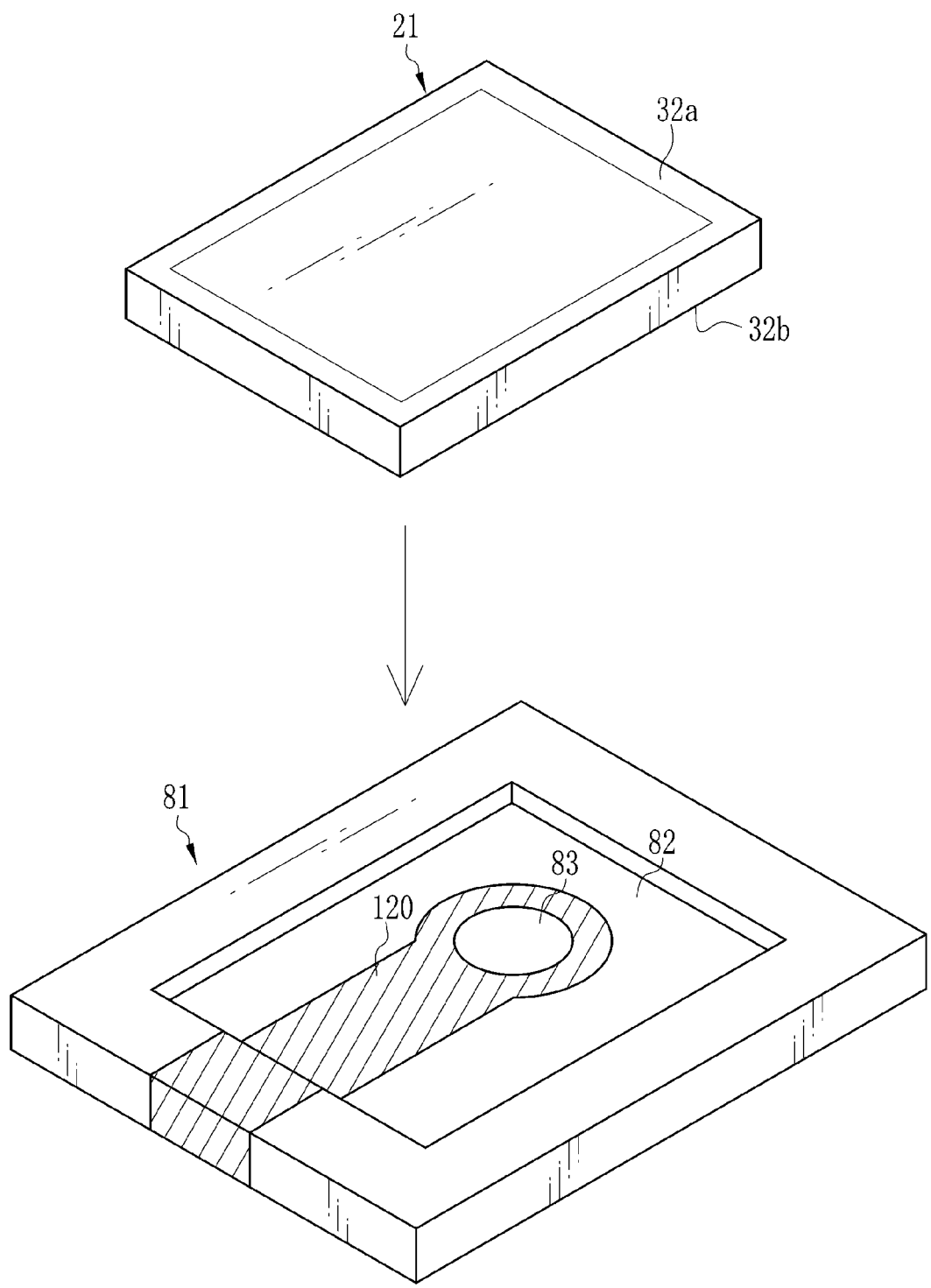

ELECTRONIC CASSETTE FOR RADIOGRAPHIC IMAGING

BACKGROUND OF THE INVENTION

1. Field of the Invention

The present invention relates to an electronic cassette for radiographic imaging. More particularly, the present invention relates to an electronic cassette for radiographic imaging which can be charged in a wireless charging method in a manner free from problems of heat dissipation and low efficiency.

2. Description Related to the Prior Art

U.S. Pat. No. 7,866,163 (corresponding to JP-A 2006-102492) discloses an electronic cassette (electronic cassette assembly) for X-ray imaging as radiographic imaging, for use in place of a conventionally used film cassette of IP cassette (imaging plate cassette). The electronic cassette receives X-rays transmitted through an object and detects an X-ray image of information of an image of the object. The electronic cassette includes a portable housing and a radiation imaging detector or FPD device (flat panel detector). The housing is in a plate shape of a small thickness. The radiation imaging detector is contained in the housing and outputs digital data of the X-ray image.

The electronic cassette is used for the X-ray imaging system installed in an imaging room in a hospital where a body (object) of a patient is positioned in an erect posture or supine posture. Also, the electronic cassette can be used discretely in a state placed on a table where the object lies, for example hands or legs, or a state manually held by the patient. Also, the electronic cassette is adapted to a portable X-ray imaging system in a site requiring emergency medicine due to an accident, disaster or the like or in a home of a patient receiving a health care service at home.

In U.S. Pat. No. 7,866,163, carbon graphite is used for a material of the housing of the electronic cassette with a small weight to increase handlability. A wireless communication interface and a rechargeable battery are contained in the housing for a wireless communication without requiring cables of communication or a power supply. The battery contained in the housing is charged by connectively setting the electronic cassette on a battery charger.

Methods of charging the battery are a contact charging method and a non-contact charging method. In the contact charging method, a connector of the housing of the electronic cassette is physically coupled to a connector of a battery charger. The non-contact charging method is disclosed in U.S. Pat. No. 7,866,163 in which the battery in the electronic cassette is rechargeable without physical contact of a connector. A technique of wireless power transmission is utilized in the non-contact charging method for charging the battery. Examples of the wireless power transmission include an electromagnetic induction method, a resonant inductive coupling method, a capacitive coupling method (field coupling method) and a radio communication method. In the electromagnetic induction method, a current flows through a power transmission coil. A power receiving coil is positioned close to the power transmission coil with a magnetic flux, and caused by the current to induce electromotive force by electromagnetic induction for generating power. In the resonant inductive coupling method, high frequency power is input to the power transmission coil, and the power is transmitted to the power receiving coil by resonance phenomenon. In the capacitive coupling method, power is transmitted by capacitive coupling between two flat plate electrodes opposed to one another. In the radio communication method, a radio wave is transmitted to and received from antennas to acquire power.

For the non-contact charging method, the housing of the electronic cassette contains a power receiving unit, which includes the power receiving coil, a flat electrode for power receiving, and a circuit device. The circuit device has a rectifier and the like and converts receiver power of an alternate current into a direct current. A wireless power transmission apparatus transmits power to the power receiving unit, and includes a power transmission unit with the power transmission coil. For charging the battery, the electronic cassette set on the wireless power transmission apparatus. The power receiving unit receives power from the wireless power transmission apparatus, and charges the battery.

JP-A 2004-252562 discloses a data processor in which the battery is charged by the radio communication method as the non-contact charging method. The housing of the data processor contains the power receiving unit having an antenna. Also, various types of the circuit device are contained in the housing with the power receiving unit. As electromagnetic noise is created by the power receiving unit, a shield device is disposed in the data processor for shielding the circuit device from the power receiving unit in order to prevent influence of the electromagnetic noise to the circuit device.

Development of use of the non-contact charging method in the electronic cassette is a presently important concern in the field of radiography. Problems have been found in the non-contact charging method in the electronic cassette in relation to a drop of efficiency in the charging and heat dissipation of the power receiving unit. Various characteristics for improving handlability of the electronic cassette are required, such as a small weight and small thickness of the housing, and durability of the housing with resistance to load of an object. Also, the housing should have a function of shielding the electromagnetic noise (electromagnetic shielding) for preventing entry of the electromagnetic noise into the housing from external electronic devices and preventing emission of the electromagnetic noise from the circuit device of the housing to the outside. Examples of materials of the housing for satisfying those requirements are carbon materials such as carbon graphite of U.S. Pat. No. 7,866,163, and metal such as stainless steel, with a small weight, high rigidity and electrical conductivity.

An electrical conductor is used as a material of the housing of the electronic cassette. The power receiving unit is contained in the housing for the non-contact charging method. For charging, the electronic cassette is set on the wireless power transmission apparatus. The electrical conductor (part of the housing) stands located between the power receiving unit and the wireless power transmission apparatus. There is formed a transmission path of power between the wireless power transmission apparatus and the power receiving unit. The electrical conductor present in the transmission path absorbs power and causes a considerably high loss of the power. A serious problem occurs in remarkable drop in the efficiency in the charging of the rechargeable battery. Although some differences occur between the plural types of the wireless power transmission, it is likely in the worst situation that all of the transmitted power is absorbed and used up for heating of the housing without use for the proper purpose of the charging.

The power receiving unit generates heat of a considerably high amount. Circuit boards irrelevant to the power receiving unit, such as a circuit board for the radiation imaging detector, do not operate in the course of the charging. Only the power receiving unit generates heat because of its circuit board. There occurs a local increase in the temperature in an active pixel area in the radiation imaging detector positioned in alignment with the power receiving unit generating heat. A difference in the temperature occurs within the active pixel area. The characteristics of the sensitivity and dark current of the pixels are changeable with dependency on the temperature. Assuming that the electronic cassette is used for imaging with the temperature difference, changes in the density occur in an X-ray image to cause failure in the imaging. Therefore, the heat dissipation should be suitably carried out for suppressing influence of heat of the power receiving unit. The housing of the electronic cassette has the small thickness. The heat dissipation must be treated as the radiation imaging detector is vulnerable to influence of the heat of the power receiving unit.

In short, there are requirements of a small weight and small thickness in the housing of the electronic cassette. The above-mentioned problems of low efficiency in the charging and heat dissipation should be treated in consideration of reduction of the weight and thickness of the housing.

U.S. Pat. No. 7,866,163 and JP-A 2004-252562 do not disclose or suggest the above-described problems or a solution of the problems. In JP-A 2004-252562, the shield device is suggested between the power receiving unit and the circuit device contained in the housing of the data processor. There is no suggestion of the housing located in the power receiving unit between the power receiving unit and the wireless power transmission apparatus.

SUMMARY OF THE INVENTION

In view of the foregoing problems, an object of the present invention is to provide an electronic cassette for radiographic imaging which can be charged in a wireless charging method in a manner free from problems of heat dissipation and low efficiency.

In order to achieve the above and other objects and advantages of this invention, an electronic cassette includes a radiation imaging detector for detecting a radiation image of an object according to radiation from the object. A battery supplies the radiation imaging detector with power. A power receiver wirelessly receives power from a wireless power transmission apparatus for charging the battery. A housing is formed from an electrical conductor, for containing the radiation imaging detector and the power receiver. A path opening is formed in the housing, and disposed in alignment with the power receiver. A cover device is formed from a material having electrical insulating property and thermal conductivity, for closing the path opening, and conducting heat of the power receiver to the housing for dissipation.

Preferably, the cover device contains at least one material.

Preferably, the cover device includes a first portion, and a second portion, attached to the first portion, and formed from a material different from a material of the first portion.

Preferably, the cover device contains synthetic resin.

Preferably, the synthetic resin contains elastomer.

Preferably, the elastomer is silicone rubber.

Preferably, the cover device contains elastomer and a plastic material.

Preferably, the power receiver includes an energy receiver for receiving electromagnetic energy from the wireless power transmission apparatus and generating the power. A circuit device supplies the battery with the power from the energy receiver. The path opening is aligned with the energy receiver and positioned centrally of the energy receiver.

Preferably, an area of the path opening is equal to or larger than a half of an area of the energy receiver.

Preferably, an area of the path opening is equal to or smaller than two times an area of the energy receiver.

In another preferred embodiment, an area of the path opening is substantially equal to an area of the energy receiver.

Preferably, a profile line of the path opening is at least partially curved.

Preferably, the path opening is circular.

In still another preferred embodiment, the path opening includes at least one inner corner, and a curved portion for curving an edge of the inner corner.

Preferably, the cover device is thermally coupled with at least one of the energy receiver and the circuit device.

Preferably, the cover device includes a cap plate for opposing to the wireless power transmission apparatus. A cover plate is disposed between the cap plate and the energy receiver, and has a higher thermal conductivity than a thermal conductivity of the cap plate. A projection is formed to project from the cover plate along an edge of the cap plate, for directing heat of the energy receiver outwards.

Preferably, furthermore, a thermal insulator is disposed between the power receiver and the radiation imaging detector in the housing, for insulation from the heat.

Preferably, the thermal insulator is a space.

Preferably, the electrical conductor contains at least one of carbon graphite and metal.

Preferably, the wireless power transmission apparatus and the power receiver operate according to one of an electromagnetic induction method, a resonant inductive coupling method, a capacitive coupling method and a radio communication method.

Consequently, an electronic cassette for radiographic imaging which can be charged in a wireless charging method in a manner free from problems of heat dissipation and low efficiency, because a cover device can function for heat dissipation of heat from a power receiver.

BRIEF DESCRIPTION OF THE DRAWINGS

The above objects and advantages of the present invention will become more apparent from the following detailed description when read in connection with the accompanying drawings, in which:

FIG. 15 is an exploded perspective view illustrating another preferred wireless power transmission apparatus.

DETAILED DESCRIPTION OF THE PREFERRED EMBODIMENT(S) OF THE PRESENT INVENTION

Figure 1:
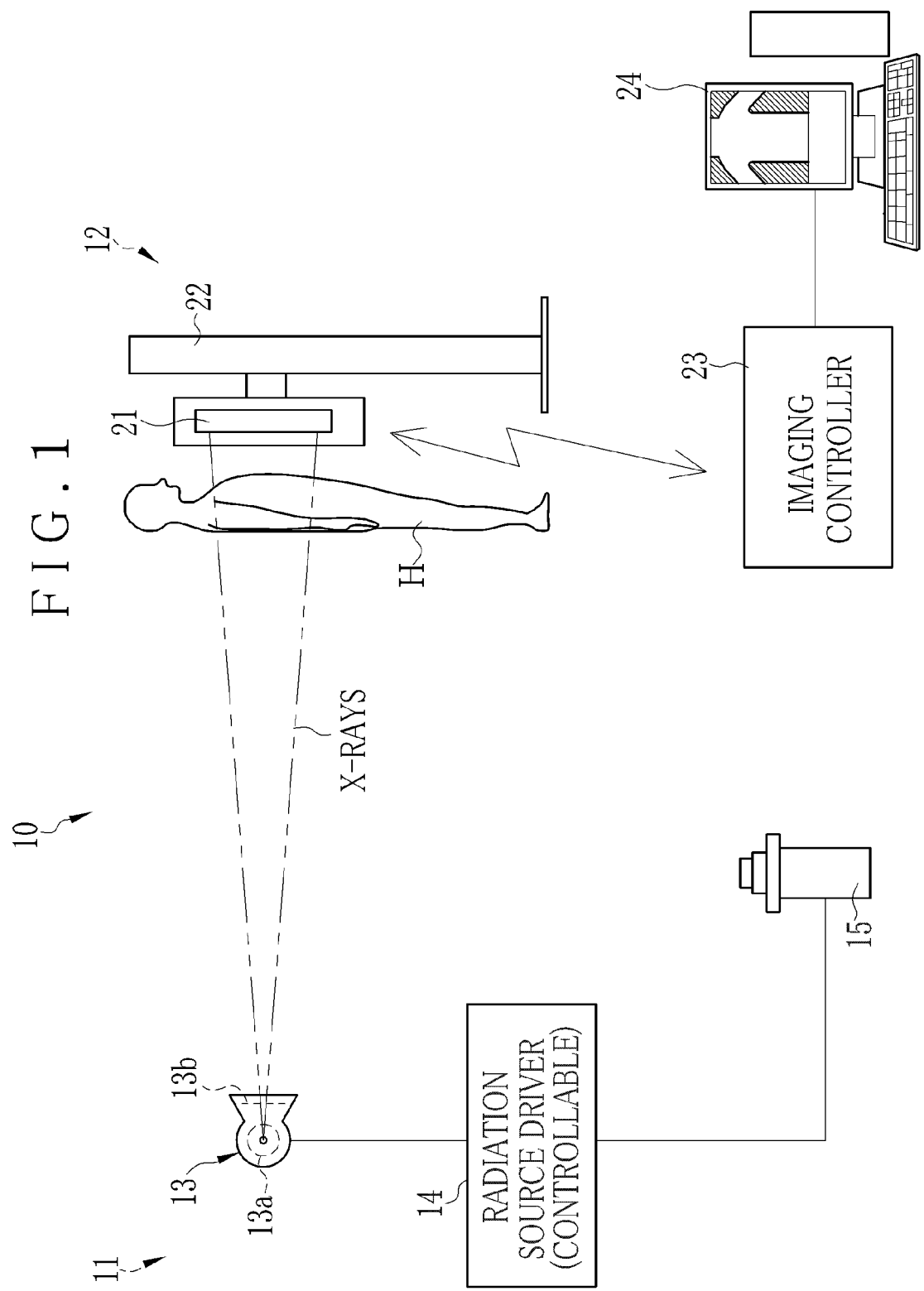
FIG. 1 is an explanatory view illustrating an X-ray imaging system.

In FIG. 1, an X-ray imaging system 10 includes an X-ray source apparatus 11 and an X-ray imaging apparatus 12. The X-ray source apparatus 11 includes an X-ray source 13, a (controllable) radiation source driver 14 and a radiation switch 15. The radiation source driver 14 controls the X-ray source 13. The X-ray source 13 includes an X-ray tube 13a and a collimator 13b for limiting a field of irradiation of X-rays emitted by the X-ray tube 13a.

The X-ray tube 13a has a cathode and an anode (target), the cathode having filaments for emitting thermal electrons, the anode undergoing collision of the thermal electrons from the cathode to emit X-rays. The collimator 13b includes four metal lead plates, which shield X-rays, are arranged in a frame form, and have an emitting opening for passing X-rays. The metal lead plates are shifted to change the sizes of the emitting opening to limit the radiation field. The four metal lead plates are combined in two pairs. Metal lead plates in each of the pairs are opposed to one another. The pairs are arranged in two directions perpendicular with one another to define the quadrilateral emitting opening.

The radiation source driver 14 includes a high voltage source and a radiation source control device. The high voltage source supplies the X-ray source 13 with high voltage. The radiation source control device controls a tube voltage, tube current and emission time. The tube voltage is a value for determining energy spectrum of X-rays emitted by the X-ray source 13. The tube current is a value for determining a radiation dose per unit time. The emission time is time of continuing emission of X-rays. The high voltage source boosts an input voltage with a transformer, generates the tube voltage as a high voltage, and supplies the X-ray source 13 with drive power by use of a high voltage cable. An imaging condition including the tube voltage, tube current and emission time is manually set by a radiology technician or operator with an input panel (not shown) of the radiation source driver 14, or by the X-ray imaging apparatus 12 through a communication cable.

The radiation switch 15 is operable by the operator, being connected to the radiation source driver 14 by a signal cable. The radiation switch 15 is a two-step switch, generates a warmup start signal for starting warming up the X-ray source 13 upon a first step of depression, and generates an emission start signal for the X-ray source 13 upon a second step of depression. Those signals are input to the radiation source driver 14 by the signal cable.

The radiation source driver 14 controls the X-ray source 13 according to a signal from the radiation switch 15. In response to the signal from the radiation switch 15 for starting emission, the radiation source driver 14 starts supplying the X-ray source 13 with power, and starts measuring time of the emission of X-rays by use of a timer. Upon a lapse of the emission time determined by the imaging condition, the radiation source driver 14 stops the emission of X-rays. The emission time varies according to the imaging condition. A longest emission time for a limit is predetermined in the radiation source driver 14 for the safety. The actual emission time in the imaging condition is determined in a range of the longest emission time.

Figure 2:
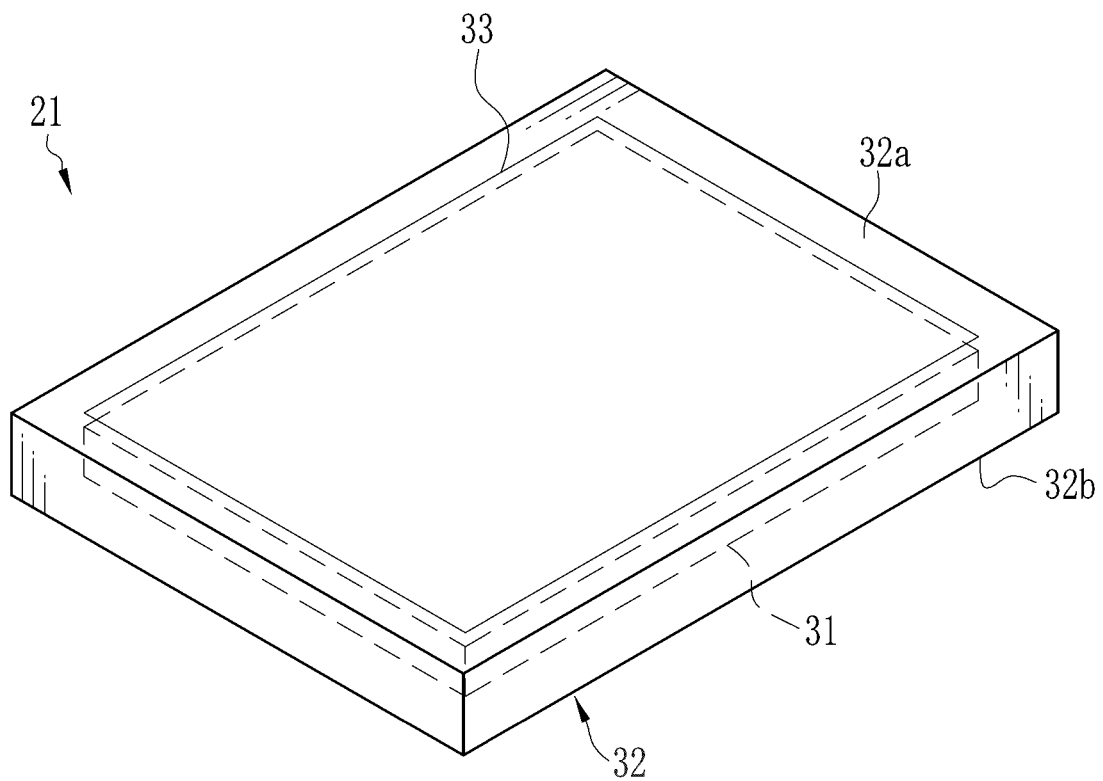
FIG. 2 is a perspective view illustrating an electronic cassette.

The X-ray imaging apparatus 12 includes an electronic cassette 21 (electronic cassette assembly), a floor stand 22, an imaging controller 23 and a console unit 24. In FIG. 2, the electronic cassette 21 includes a radiation imaging detector 31 or FPD device (flat panel detector) and a portable housing 32 for containing the radiation imaging detector 31. The electronic cassette 21 is a radiographic imaging assembly of a portable type for receiving X-rays transmitted through an object H (patient's body) after emission from the X-ray source 13, and creating an X-ray image of the object H. The housing 32 of the electronic cassette 21 has a shape of a flat plate with a small thickness. A flat size of the housing 32 is approximately equal to that of a film cassette and IP cassette. A front surface 32a and a rear surface 32b are quadrilateral. A radio-transparent front plate 33 constitutes the front surface 32a for receiving entry of X-rays.

In FIG. 1, the floor stand 22 has a slot for mounting the electronic cassette 21 in a removable manner, and keeps the electronic cassette 21 oriented to direct the front surface 32a to the X-ray source 13. As the size of the housing 32 is equal to that of a film cassette or IP cassette, the electronic cassette 21 is mountable on a floor stand for imaging with the film cassette or IP cassette. Note that the floor stand for imaging the object H in an erect posture is illustrated, but an imaging table for imaging the object H in a supine posture can be used. Furthermore, the electronic cassette 21 can be used separately from the floor stand 22 typically in the case of imaging parts of the body of the object H difficult to image in the condition mounted on the floor stand 22, for example, hands and legs. Also, the electronic cassette 21 may not be used in an imaging room. For example, a medical cart (portable type of X-ray imaging apparatus) together with the electronic cassette 21 can be carried into a hospital room of a patient, so as to use the electronic cassette 21 at a bed in the hospital room.

Figure 3:
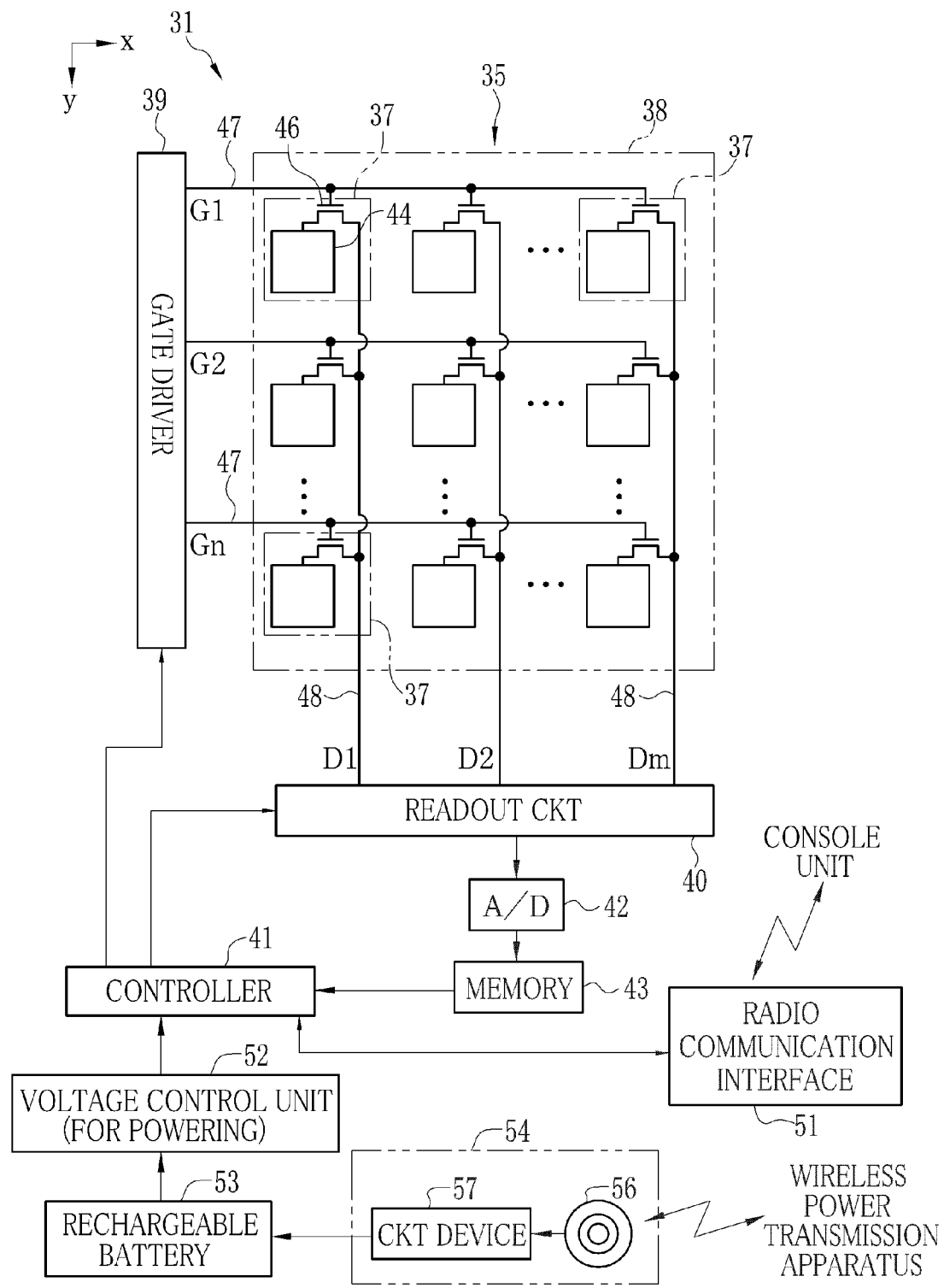
FIG. 3 is a block diagram schematically illustrating a radiation imaging detector or FPD device (flat panel detector)

The electronic cassette 21 is a wireless device. In FIG. 3, a radio communication interface 51 of the electronic cassette 21 communicates with the imaging controller 23. A battery supplies power to drive the electronic cassette 21. Handlability of the electronic cassette 21 of the wireless type is good because no communication cable or power supply cable is necessary.

The imaging controller 23 is kept communicable with the electronic cassette 21 in a wireless manner, and controls the electronic cassette 21. Specifically, the imaging controller 23 transmits information of an imaging condition to the electronic cassette 21, for the electronic cassette 21 to set a condition of signal processing in the radiation imaging detector 31, for example, for an output gain of an integrating amplifier for amplifying a voltage according to a signal charge. Also, the imaging controller 23 receives a sync signal from the X-ray source apparatus 11 for synchronizing emission of the X-ray source 13 with storage of the radiation imaging detector 31, and transmits the sync signal to the electronic cassette 21 for the sync control between the X-ray source 13 and the radiation imaging detector 31. The imaging controller 23 receives image data output by the electronic cassette 21, and sends the image data to the console unit 24.

The console unit 24 receives information of an examination request of the patient, such as sex, age, body part, purpose of imaging, and the like, and causes the display panel to display the information of the examination request. The examination request information is originally supplied by an outer system for managing patient information or diagnosis information, such as the HIS (Hospital Information System)

and RIS (Radiography Information System). Also, the examination request information can be input by an operator or technician manually. He or she observes the examination request information on the display panel, and selectively determines an imaging condition according to the same by viewing images on the console unit 24. The selected imaging condition is transmitted to the imaging controller 23.

The console unit 24, besides the transmission of the information of the imaging condition, processes data of X-ray image received from the imaging controller 23 in the image processing. The processed X-ray image is displayed on a display panel of the console unit 24. Image data of the X-ray image is stored in a data storage device, such as a hard disk and memory of the console unit 24, a storage server connected to the console unit 24 by the network, and the like.

In FIG. 3, the radiation imaging detector 31 includes a detection panel 35, a gate driver 39, a readout circuit 40, a controller 41, an A/D converter 42 and a memory 43. An active pixel area 38 is disposed on the detection panel 35. Plural pixels 37 are arranged in the active pixel area 38 in plural arrays for storing a signal charge according to a radiation dose of incident X-rays. The detection panel 35 creates an X-ray image. The gate driver 39 drives the pixels 37 and controls the readout of the signal charge. The readout circuit 40 reads out the signal charge from the pixels 37. The controller 41 controls the various elements. The A/D converter 42 converts the signal charge being read out into digital data. The converted data from the A/D converter 42 are written to the memory 43. The pixels 37 are arranged in arrays G1-Gn (direction x) and columns D1-Dm (direction y) at a predetermined pitch.

Figure 4:
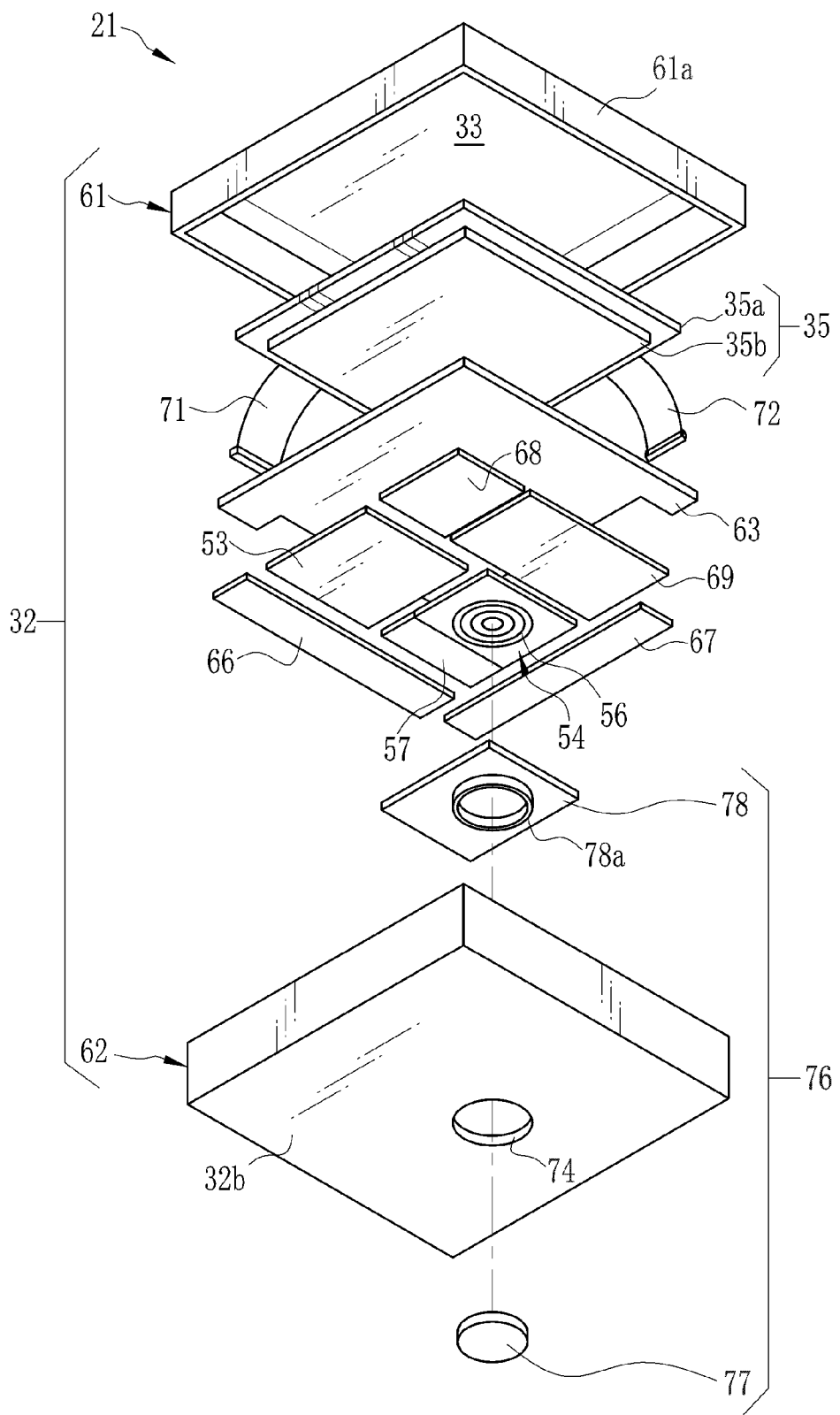
FIG. 4 is an exploded perspective view illustrating the electronic cassette.
Figure 5:
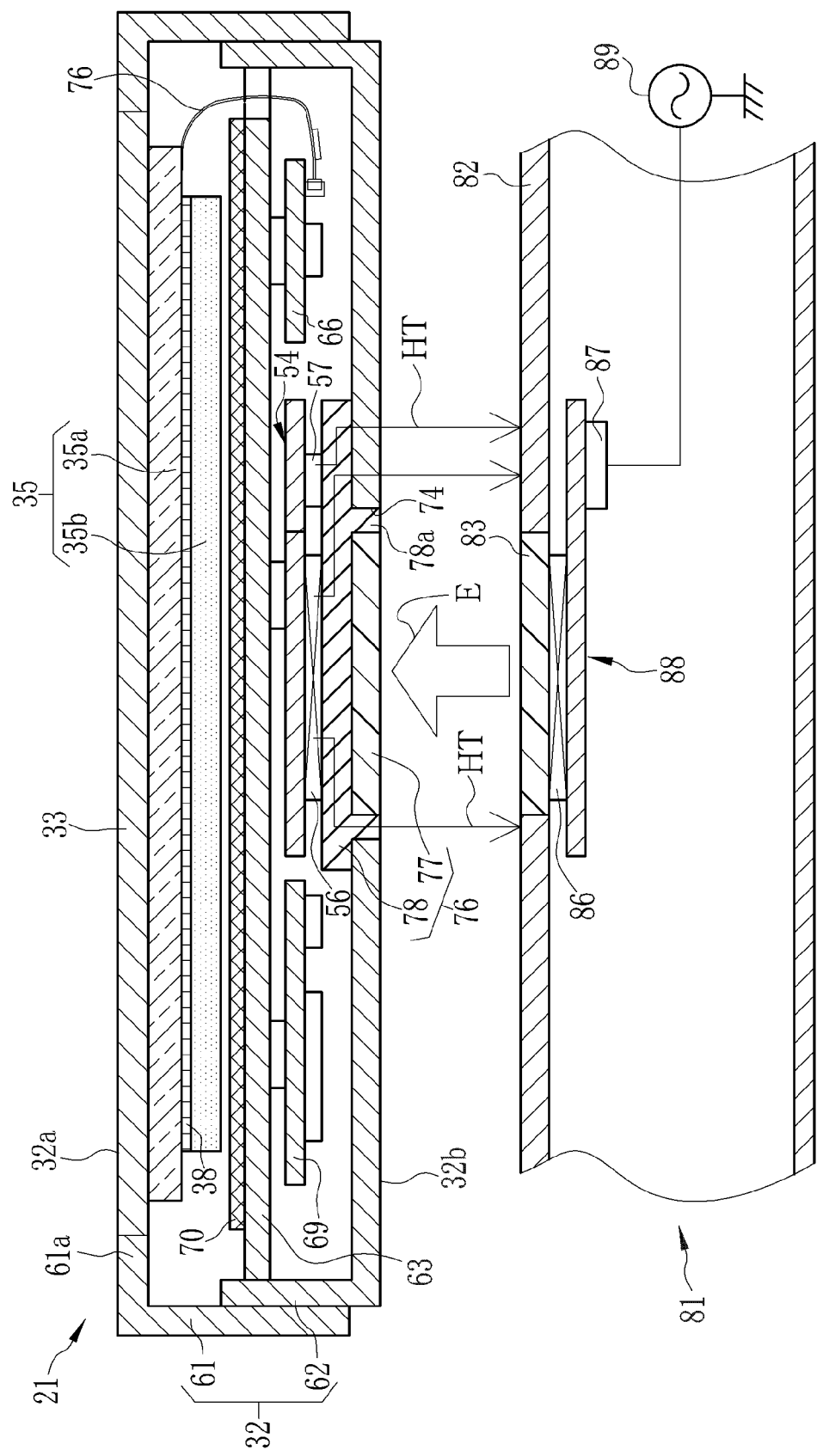
FIG. 5 is a cross section illustrating the electronic cassette and the wireless power transmission apparatus.

The detection panel 35 is an indirect conversion type for converting X-rays into visible light, converting the visible light photoelectrically into a signal charge, and storing the signal charge. The detection panel 35 includes a photoconductive film 35a and a scintillator 35b as illustrated in FIGS. 4 and 5. There is a glass substrate or insulating substrate. The active pixel area 38 is defined by arranging the pixels 37 on the glass substrate. The photoconductive film 35a photoelectrically converts the visible light at the pixels 37. The scintillator 35b extends to cover the entirety of the active pixel area 38.

The scintillator 35b is phosphor, such as CsI (cesium iodide) and GOS (gadolinium oxysulfide), and converts X-rays into visible light. The scintillator 35b is formed by one of various methods including attachment of a sheet coated with phosphor to a panel with adhesive agent, and vapor deposition of the phosphor on the active pixel area 38.

Each of the pixels 37 includes a photo diode 44 and a thin film transistor 46 (TFT) as a switching element. The photo diode 44 is a photoconductor for generating charge (electron-hole pairs) upon entry of visible light. The photo diode 44 has a structure including a semiconductor layer such as a-Si (amorphous silicon), for example, of the PIN type, and upper and lower electrodes formed on the semiconductor layer. The TFT 46 is connected to the lower electrode of the photo diode 44. A bias voltage is applied to the upper electrode. An electric field is created in the semiconductor layer in the photo diode 44 by the application of the bias voltage. Charge generated in the semiconductor layer by the photoelectric conversion (electron-hole pairs) is moved to the upper and lower electrodes of which one has a positive polarity and the other has a negative polarity. The photo diode 44 operating as a capacitor stores the charge. Note that the detection panel 35 may be a direct conversion type for converting X-rays into charge directly in place of the indirect conversion type.

The TFTs 43 have electrodes of a gate, source and drain. A scan line 47 is connected with the gate of the TFTs 43. A signal line 48 is connected with the source. Each of the photo diodes 44 is connected with the drain. The scan lines 47 and the signal lines 48 are disposed in a form of a grating. A number of the scan lines 47 is n or the array number of the pixels 37 in the active pixel area 38. A number of the signal lines 48 is m or the column number of the pixels 37. The scan lines 47 are connected to the gate driver 39. The signal lines 48 are connected to the readout circuit 40.

The readout circuit 40 includes an integrating amplifier and a multiplexer. The integrating amplifier converts the signal charge read from the detection panel 35 into a voltage signal. The multiplexer serially changes over the arrays of the pixels 37 in the active pixel area 38 and outputs a voltage signal of each array. The voltage signal read out by the readout circuit 40 is converted into digital image data by the A/D converter 42. The digital image data is written to the memory 43.

A voltage control unit 52 (for powering), a rechargeable battery 53 and a power receiver 54 or power receiving unit are contained in the housing 32 with the radio communication interface 51. The radio communication interface 51, the voltage control unit 52 and the power receiver 54 are controlled by the controller 41. The radio communication interface 51 wirelessly communicates with the console unit 24 by use of a radio wave, light (infrared rays) and the like. The image data read from the memory 43 is transmitted by the radio communication interface 51 to the console unit 24.

The voltage control unit 52 supplies circuit elements of the radiation imaging detector 31 with power from the battery 53. The voltage control unit 52 includes a DC-DC converter for converting a voltage of the direct current from the battery 53 into a voltage of a value in compliance with the circuit elements. The battery 53 is a rechargeable secondary battery connected to the power receiver 54. Other examples of the battery 53 can be an electric double layer capacitor, lithium ion capacitor and other rechargeable battery for operating suitably as a power source for the electronic cassette 21.

A wireless power transmission apparatus 81 or wireless power source (wireless battery charger) in the power transfer of FIG. 5 wirelessly transmits power to the power receiver 54 for charging the battery 53. An example of the wireless power transmission from the wireless power transmission apparatus 81 to the power receiver 54 is an electromagnetic induction method. The power receiver 54 includes a power receiving coil 56 or secondary inductive coil (energy receiver) and a circuit device 57 (power output device). The power receiving coil 56 receives power from the wireless power transmission apparatus 81. A power transmission coil 86 or primary inductive coil (energy transmitter) of FIG. 5 is incorporated in the wireless power transmission apparatus 81. In case an alternate current flows in the power transmission coil 86 while the power transmission coil 86 is aligned with the power receiving coil 56, then electromotive force is induced in the power receiving coil 56 by electromagnetic induction with a magnetic flux. The circuit device 57 includes a rectifier for converting an alternate current of power in the power receiving coil 56 to a direct current, and supplies the battery 53 with the power of the direct current.

In FIGS. 4 and 5, the housing 32 includes a front housing shell 61 and a rear housing shell 62. The front housing shell 61 has a plastic frame 61a and the front plate 33 attached to an opening of the frame 61a. The frame 61a is formed from an electrically conductive plastic material containing resin and electrically conductive filler mixed in the resin. The front plate 33 is formed from carbon graphite. An example of material for the rear housing shell 62 is metal, such as stainless steel. The electronic cassette 21 is required to have a lightweight property for easy handlability, and also durability sufficient for load of the object H. Thus, preferred examples of materials of the housing 32 are carbon graphite, magnesium alloy, aluminum, aluminum alloy and the like with a small weight and high rigidity.

Various materials in the housing shells 61 and 62 of the housing 32 are all electrically conductive, including the electrically conductive plastic material, carbon graphite and metal. The housing 32 is an electromagnetic shield for blocking electromagnetic noise created inside or outside the housing 32. Note that the materials for constituting the housing 32 are not limited to the embodiment. For example, the entirety of the housing 32 can be formed from carbon graphite.

In the electronic cassette 21, the detection panel 35 is disposed in a type of "Irradiation Side Sampling (ISS)" in which the photoconductive film 35a and the scintillator 35b are arranged in a direction of an optical path of X-rays. In the ISS type, a receiving surface of the scintillator 35b where the efficiency in the conversion from X-rays to visible light is opposed to the active pixel area 38 of the photoconductive film 35a. Efficiency in detecting X-rays is high. The detection panel 35 is attached to an inner surface of the front housing shell 61 with adhesive agent or double sided tape by orienting the scintillator 35b toward the rear housing shell 62. Note that the arrangement of the detection panel 35 may not be the ISS type, but can be a type of "Penetration Side Sampling (PSS)" in which the scintillator 35b and the photoconductive film 35a are arranged in the direction of an optical path of X-rays.

A support plate 63 is disposed behind the detection panel 35. Circuit boards 66, 67, 68 and 69 are mounted on the support plate 63 together with the battery 53 and the power receiver 54. An example of material of the support plate 63 is stainless steel. Also, the support plate 63 prevents X-rays from entry to the circuit boards 66-69 and the power receiver 54. A thermal insulator 70 of FIG. 5 is disposed in front of the support plate 63 to extend between the scintillator 35b and the front housing shell 61. The thermal insulator 70 prevents heat of the circuit boards 66-69 and the power receiver 54 from conducting to the detection panel 35. An example of the thermal insulator 70 is a sponge sheet or porous sheet.

The circuit board 66 has circuit elements constituting the gate driver 39 to drive the TFTs in the detection panel 35. The circuit board 67 has circuit elements constituting the readout circuit 40. Flexible wiring boards 71 and 72 connect the circuit boards 66 and 67 to the detection panel 35. Each of the flexible wiring boards 71 and 72 has an IC chip (not shown) of a tape carrier package type (TCP). The IC chip constitutes the gate driver 39 and the readout circuit 40 together with the circuit elements in each of the circuit boards 66 and 67.

The circuit board 68 constitutes the voltage control unit 52. The circuit board 69 has circuit elements of the A/D converter 42, the controller 41 and the radio communication interface 51. The circuit boards 66, 67 and 68 are connected to the circuit board 69 by wiring. The battery 53 is connected with the power receiver 54 and the circuit board 68 by wiring, connectors and the like.

A cover plate 78 is disposed between the power receiver 54 and the rear housing shell 62. A cap 77 or cap plate (path plate) is combined with the cover plate 78 to constitute a cover device 76. A path opening 74 is formed in the rear housing shell 62 and positioned at the power receiving coil 56 of the power receiver 54. The cover device 76 is as a dust-proof structure for closing the path opening 74 to prevent dust, particles or the like from entry in the housing 32.

Figure 6:
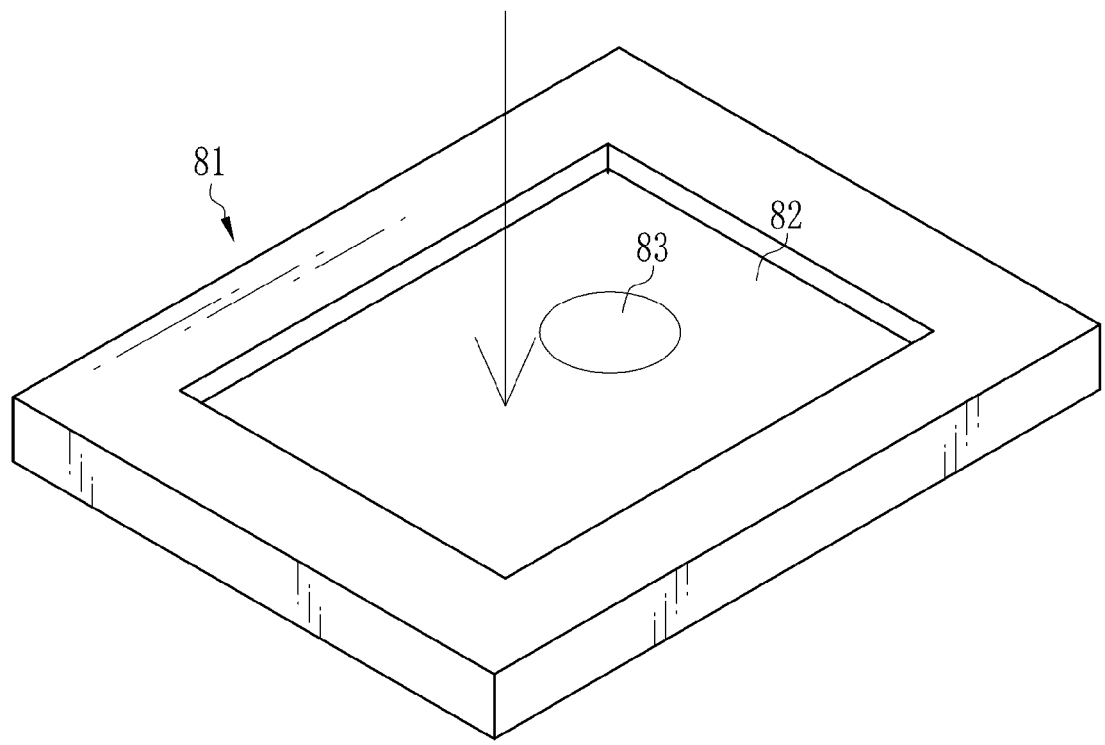
FIG. 6 is a perspective view illustrating setting of the electronic cassette on the wireless power transmission apparatus.

The wireless power transmission apparatus 81 has a holder plate 82 (support wall) and a path window 83 (path wall). In FIG. 6, in case the electronic cassette 21 is set on the holder plate 82, the path opening 74 is aligned with the path window 83 (path wall) of the wireless power transmission apparatus 81. In FIG. 5, the path opening 74 prevents a loss in the power E transmitted from the wireless power transmission apparatus 81. A power transmitter 88 in the wireless power transmission apparatus 81 is constituted by a power transmission circuit 87 (power input device) and the power transmission coil 86. An alternate current power source 89 of a commercial system is connected with the power transmission circuit 87 by a power supply cable.

The power transmission coil 86 is disposed directly inside the path window 83 (path wall). In case the electronic cassette 21 is set in the wireless power transmission apparatus 81, the power transmission coil 86 is aligned with the power receiving coil 56 closely so that the path window 83 (path wall) and the path opening 74 are located between those. The power transmission circuit 87 inputs power of an alternate current to the power transmission coil 86. In case an alternate current flows in the power transmission coil 86 as a primary current, electromagnetic induction occurs to generate a secondary current in the power receiving coil 56 with a magnetic flux, to induce power of the alternate current. Thus, the power E is wirelessly transmitted from the wireless power transmission apparatus 81 to the power receiver 54.

As described heretofore, the housing 32 is formed from the electrical conductor. Assuming that the electrical conductor is disposed in the transmission path of the power E, a loss in the power occurs due to absorption of the power E in the housing 32 and consumption in heating the housing 32. The loss decreases the efficiency in the charging of the battery 53 with the power receiver 54. In view of this, the path opening 74 is formed in the rear housing shell 62 in its portion disposed in the transmission path of the power E and aligned with the power receiving coil 56 by partial retraction. Materials for the cover device 76 to close the path opening 74 and the path window 83 (path wall) are electrical insulating material. Therefore, no electrical conductor is present in the transmission path of the power E. No loss of power due to the electrical conductor occurs. The efficiency in the charging the battery 53 can be prevented from decreasing. In the present description, the electrical insulating property is defined as a property of having electrical resistance equal to or higher than 1 MΩ as measured according to JIS K6271.

The path opening 74 is circular in compliance with the shapes of the power receiving coil 56 and the power transmission coil 86 as viewed vertically. A diameter of the path opening 74 is approximately equal to that of the power receiving coil 56 and the power transmission coil 86. The structure with the path opening 74 formed in the rear housing shell 62 has a lower performance of electromagnetic shielding for the circuit boards 66-69 in the housing 32 than a structure without the path opening 74. However, the path opening 74 is positioned at the power receiving coil 56. Thus, a decrease in performance of electromagnetic shielding of the housing 32 can be sufficiently small for the circuit boards 66-69. Note that it is possible to dispose a shielding structure between the power receiver 54 and the circuit boards 66-69 inside the housing 32 as disclosed in JP-A 2004-252562 for the purpose of compensating for a decrease in the performance of electromagnetic shielding with the path opening 74.

The cover device 76, in addition to preventing entry of dust, particles or the like from the path opening 74, transmits heat HT of the power receiver 54 to the housing 32. Thus, the cover device 76 is a heat dissipator for dissipating the heat of the power receiver 54.

An amount of heat generated by the power receiver 54 is higher than that of heat generated by the circuit boards 66-69. While the battery 53 is charged by setting the electronic cassette 21 in the wireless power transmission apparatus 81, only the power receiver 54 generates heat, as the circuit boards 66-69 do not operate. Then temperature of a portion of the active pixel area 38 of the detection panel 35 corresponding to the power receiver 54 rises locally to create a difference in the temperature within the active pixel area 38. As characteristics of the sensitivity and dark current of the pixels 37 are changed with dependency on the temperature, the temperature difference becomes apparent as changes in the density in the X-ray image. Assuming that the electronic cassette 21 is used with the temperature difference in the active pixel area 38 after charging the battery 53 without sufficient natural cooling with time, changes in the density occur in the X-ray image in an unwanted manner due to the heat generated in the power receiver 54. In consideration of this situation, heat is dissipated from the power receiver 54 by the cover device 76, to suppress an increase in the temperature in the active pixel area 38 with the power receiver 54.

The cover device 76 is formed from material with electrical insulating property and thermal conductivity. The thermal conductivity is defined as a property having a thermal conductivity value equal to or higher than 0.1 W/m·K as measured according to the hot disk method. An example of the material of the cover plate 78 is silicone rubber. The silicone rubber is a synthetic resin or elastomer having electrical insulating property and thermal conductivity, and also resiliency. The cover plate 78 has such a size as to cover the entirety of the power receiver 54 as viewed horizontally. A surface of the cover plate 78 opposed to the power receiver 54 contacts the entirety of the power receiver 54. Consequently, the cover plate 78 is thermally coupled with the power receiving coil 56 and the circuit device 57 as a heat source of the power receiver 54. The heat HT from the power receiver 54 is conducted to the cover plate 78.

The temperature of the power receiving coil 56 and the circuit device 57 rises as high as 70-80 degrees Centigrade by heat from the power receiver 54. As the silicone rubber is highly resistant to heat, the structure of the silicone rubber is appropriate for portions to contact the power receiver 54 generating much heat. Examples of silicone rubber include vinyl methyl silicone rubber (VMQ), phenylmethyl silicone rubber (PMQ), and the like. Vinyl methyl silicone rubber has a very small change in the characteristic in a large temperature range from −60 to 250 degrees Centigrade, and has high resistance to heat and high resistance to cold. Phenylmethyl silicone rubber has still higher performance in the low temperature than vinyl methyl silicone rubber. Brittle temperature of phenylmethyl silicone rubber is as low as −115 degrees Centigrade. The silicone rubber has a break down voltage of 500-1,100 V/mm at which insulation is broken, and is highly resistant to electric charge. Thus, structure of the silicone rubber is appropriate for portions to contact the power receiver 54 as an electric part. A preferred example of material for the cover device 76 is vinyl methyl silicone rubber of a general purpose material. It is possible in the cover device 76 to use phenylmethyl silicone rubber or else a fluorinated silicone rubber (FVMQ) other than vinyl methyl silicone rubber and phenylmethyl silicone rubber on the condition of satisfying the required resistance to heat and electric charge.

Also, a circular sealing ridge projection 78a is formed on a surface of the cover plate 78 opposed to the rear housing shell 62, and entered in the path opening 74. A shape and diameter of the ridge projection 78a are equal to those of the path opening 74 for its peripheral surface to contact an inner surface of the path opening 74 tightly.

A surface of the cover plate 78 opposed to the rear housing shell 62 contacts a peripheral portion of the path opening 74 in the rear housing shell 62 around the ridge projection 78a. Thus, the cover plate 78 is thermally coupled with the rear housing shell 62. The power receiver 54 is thermally coupled with the rear housing shell 62 by the cover plate 78. The heat HT of the power receiver 54 is transmitted to the rear housing shell 62 by the cover plate 78.

Owing to the rear housing shell 62 of stainless steel, the heat HT transmitted from the cover plate 78 to the rear housing shell 62 is dispersed within the rear housing shell 62 and dissipated to the outside of the housing 32. Specifically, the heat HT is dissipated to the atmosphere through an outer portion of the rear housing shell 62 contacting the atmosphere. Also, while the electronic cassette 21 is set on the wireless power transmission apparatus 81, the rear housing shell 62 contacts the holder plate 82. Thus, the heat HT conducts from the rear housing shell 62 to the holder plate 82. Portions of the holder plate 82 other than the path window 83 (path wall) are formed from a material of high thermal conductivity, such as metal, similar to the rear housing shell 62. Thus, the heat HT flows from the rear housing shell 62 to the holder plate 82.

The cap 77 is fitted in the ridge projection 78a. The cap 77 is formed from a hard plastic material (synthetic resin) with a higher hardness than the silicone rubber in the cover plate 78. The cap 77 is circular in compliance with the path opening 74 and the ridge projection 78a. The ridge projection 78a operates as a packing or seal for enclosing the path opening 74 by tightly closing a gap between the cap 77 and the path opening 74.

The cap 77 reinforces the housing 32 with rigidity even in the presence of the path opening 74. Incase the cap 77 is secured to the path opening 74, a surface of the cap 77 becomes an outer surface of the rear housing shell 62 in the path opening 74. As a friction coefficient of the cap 77 is lower than that of silicone rubber, a slipping property of the rear housing shell 62 is increased at the path opening 74 by the cap 77. Thus, entry of the electronic cassette 21 between the imaging table (bed) and the object H can be facilitated.

Also, the plastic material for the cap 77 is thermally conductive, and operates as a heat dissipator for dissipating heat HT to the outside of the housing 32. Note that the cap 77 contacts the path window 83 (path wall). The path window 83 (path wall) is formed from a plastic material, and has a lower thermal conductivity than a peripheral portion of metal of the holder plate 82 around the path window 83 (path wall). An amount of dissipated heat conducted through the cap 77 and the path window 83 (path wall) is smaller than that of dissipated heat conducted through the cover plate 78.

In other words, thermal conductivity of the cap 77 and the path window 83 (path wall) formed from the hard plastic material is lower than thermal conductivity of the cover plate 78 of silicone rubber.

The operation of the above construction is described now. To use the electronic cassette 21 for the radiography in the X-ray imaging system 10, at first the electronic cassette 21 is set on the holder plate 82 (support wall) of the wireless power transmission apparatus 81 or wireless power source (wireless battery charger) in FIG. 6, to charge the rechargeable battery 53. The electronic cassette 21 is so disposed that the rear surface 32b is directed to the holder plate 82. In response, the path window 83 (path wall) of the wireless power transmission apparatus 81 is aligned with the path opening 74 of the electronic cassette 21, to align the power transmission coil 86 or primary inductive coil (energy transmitter) with the power receiving coil 56 or secondary inductive coil (energy receiver).

In case the power transmission circuit 87 (power input device) starts supplying the power transmission coil 86 with power of an alternate current as illustrated in FIG. 5, the power receiver 54 starts charging the battery 53. As the alternate current flows in the power transmission coil 86, power of the alternate current is induced in the power receiving coil 56 by electromagnetic induction. Thus, the wireless power transmission apparatus 81 supplies the power receiver 54 with power E (electromagnetic energy). The power induced in the power transmission coil 86 is converted by the circuit device 57 into power of a direct current, which is supplied to the battery 53. See FIGS. 3 and 4.

In FIG. 5, the path window 83 (path wall), the path opening 74 and the cover device 76 are aligned together in a transmission path of power E. As the path window 83 (path wall) and the cover device 76 are formed from the electrical insulating material, no electrical conductor is present in the transmission path of power E. Thus, high efficiency in the charging is ensured because no loss in the power occurs with an electrical conductor.

In case the power receiver 54 is supplied with the power E, the power receiver 54 generates heat. The heat HT of the power receiver 54 is transmitted by the cover device 76 and dissipated in the housing 32 and the holder plate 82. The cover plate 78, because formed from silicone rubber with resiliency, is resiliently deformed according to shapes of surfaces of the power receiving coil 56 and the circuit device 57, and tightly contacts those. Also, tight contact occurs between the cover plate 78 and the rear housing shell 62. This increases a pressure of the contact and an area of the contact. High thermal conductivity can be ensured in comparison with a comparison example having the cover plate 78 formed from a rigid material without resiliency even with an equal thermal conductivity.

In case the battery 53 is charged completely, the electronic cassette 21 is removed from the wireless power transmission apparatus 81. While the battery 53 is charged, the heat HT of the power receiver 54 is dissipated by the cover device 76. The temperature of the active pixel area 38 is prevented from increasing even with the heat HT upon completion of charging the battery 53.

For imaging with the electronic cassette 21 in the X-ray imaging system 10, the electronic cassette 21 and the object H are positioned relative to one another by setting the electronic cassette 21 on the floor stand 22 or placing the electronic cassette 21 on an imaging table (bed). As the path opening 74 of the housing 32 is closed by the cover device 76, entry of dust, particles or the like is prevented in the path opening 74.

The cover plate 78 is formed from resilient silicone rubber, and tightly contacts the housing 32. The cover plate 78 closes the path opening 74 in a fluid-tight manner effectively with fluid-proof and drip-proof property. In the case of discrete use of the electronic cassette 21 without mounting on the floor stand 22, the housing 32 contacts the object H upon positioning and imaging. Fluid such as body fluid and blood of the body or object H is likely to deposit on an outer surface of the housing 32. However, the path opening 74 is enclosed by the cover plate 78, to prevent the fluid from entry in the housing 32 through the path opening 74. Also, the ridge projection 78a is formed on the cover plate 78 to seal the gap between the cap 77 and the path opening 74, to obtain the highly drip-proof property.

After the positioning, the X-ray source apparatus 11 emits X-rays to create an X-ray image. The electronic cassette 21 is synchronized with emission of the X-rays. The radiation imaging detector 31 is powered by the battery 53 and creates the X-ray image. No influence of electromagnetic noise occurs to the radiation imaging detector 31, as the housing 32 operates as an electromagnetic shield. The X-ray image is transmitted from the electronic cassette 21 to the console unit 24. Influence of the heat HT of the power receiver 54 to the active pixel area 38 is suppressed by the cover device 76 for heat dissipation. The form of the X-ray image can be free from changes in the density due to the heat HT.

As described heretofore, the housing 32 of the electrical conductor in the electronic cassette 21 of the invention has the path opening 74 in the portion aligned with the power receiver 54 for a transmission path of power E. The cover device 76 for closing the path opening 74 is formed from the electrical insulating material. Thus, efficiency in charging with the power receiver 54 can be kept without dropping.

Also, heat of the power receiver 54 can be dissipated easily by the use of the thermally conductive material in the cover device 76. It is possible to reduce the weight and thickness of the housing 32 in comparison with a combination of the cover device 76 and a heat dissipator additional to the cover device 76. Assuming that such an additional heat dissipator is combined with the cover device 76, it is possible to reduce weight and thickness of the additional heat dissipator owing to the use of the cover device 76. The housing 32 can be constructed still more compactly.

In the present embodiment, the cover plate 78 of the cover device 76 is formed from resilient silicone rubber. Thus, drip-proof property can be obtained as well as the dust-proof property. The cover device 76 is the composite device including the cover plate 78 and the cap 77 formed from a plastic material with a higher rigidity than the silicone rubber. Thus, the rigidity can be ensured in comparison with a structure without the cap 77.

In the above embodiments, silicone rubber is used for the cover plate 78. However, other elastomers can be used. An example of the elastomer is a synthetic rubber, such as nitrile butadiene rubber (NBR). The nitrile butadiene rubber has a smaller resistance to heat (approximately 130 degrees Centigrade) than silicone rubber, but higher thermal conductivity. Consequently, it is preferable to use silicone rubber for the purpose of high resistance to heat, and to use the nitrile butadiene rubber for the purpose of high performance for heat dissipation.

Other examples of elastomers different from silicone rubber and NBR can be also used on a condition of having characteristics important for heat dissipation of the power receiver 54, such as resistance to heat and thermal conductivity. The use of an elastomer can ensure the drip-proof property with resiliency. Also, forming the cover plate 78 from elastomer is effective in omitting packing or sealing material specialized for obtain a drip-proof property. The number of the parts can be set small.

In the above embodiment, the wireless power transmission between the wireless power transmission apparatus 81 and the power receiver 54 is the electromagnetic induction method. However, other examples of the wireless power transmission can be used, such as a resonant inductive coupling method, a capacitive coupling method (field coupling method) and a radiocommunication method. In the resonant inductive coupling method, high frequency power is input to a transmission coil, and the power is transmitted to a receiving coil by resonance phenomenon. In the capacitive coupling method, power is transmitted by capacitive coupling between two flat plate electrodes opposed to one another. In the radio communication method, a radio wave is transmitted to and received from antennas to acquire power.

In the resonant inductive coupling method, a wireless power transmission apparatus has a transmission coil as the power transmitter. The electronic cassette has a receiving coil as the power receiver similar to the above embodiments. The transmission path is defined between the transmission coil and the receiving coil where a magnetic field is created. In the capacitive coupling method, a wireless power transmission apparatus has a first flat electrode as the power transmitter (energy transmitter). The electronic cassette has a second flat electrode as the power receiver (energy receiver). The transmission path is defined between the first and second flat electrodes where an electric field is created. In the radio communication method, a wireless power transmission apparatus has a first antenna as the power transmitter (energy transmitter). The electronic cassette has a second antenna as the power receiver (energy receiver). The transmission path is defined between the first and second antennas where radio communication is carried out. In any one of those methods, the feature of the invention is effective because no electrical conductor is present in the transmission path to keep efficiency in charging the battery 53 without drop.

Figure 7:
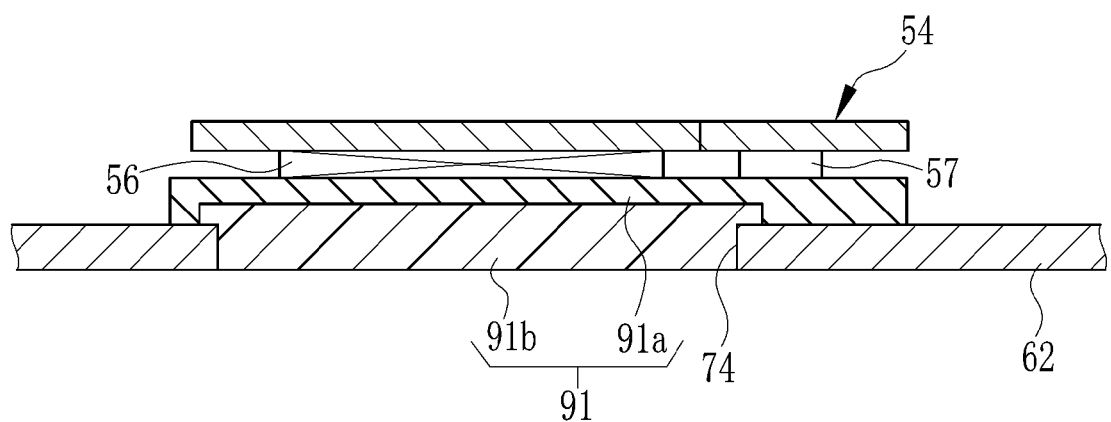
FIG. 7 is a cross section illustrating another preferred cover device including plural modified components.

In FIGS. 7-10, other preferred cover devices are illustrated. In FIG. 7, a cover device 91 includes a cover plate 91a and a cap 91b or cap plate (path plate). No ridge projection is formed on the cover plate 91a of the cover device 91 for entry in the path opening 74. The cap 91b is formed with a larger diameter as a difference from the cover device 76 of FIG. 5. The material of the cover device 76 is repeated in the cover plate 91a and the cap 91b of the cover device 91. As the cover plate 91a is formed from elastomer such as silicone rubber, the inner surface of the rear housing shell 62 of the housing 32 is kept in tight contact with the cover plate 91a even without a ridge projection. The cover device 91 can have a drip-proof structure.

Figure 8:
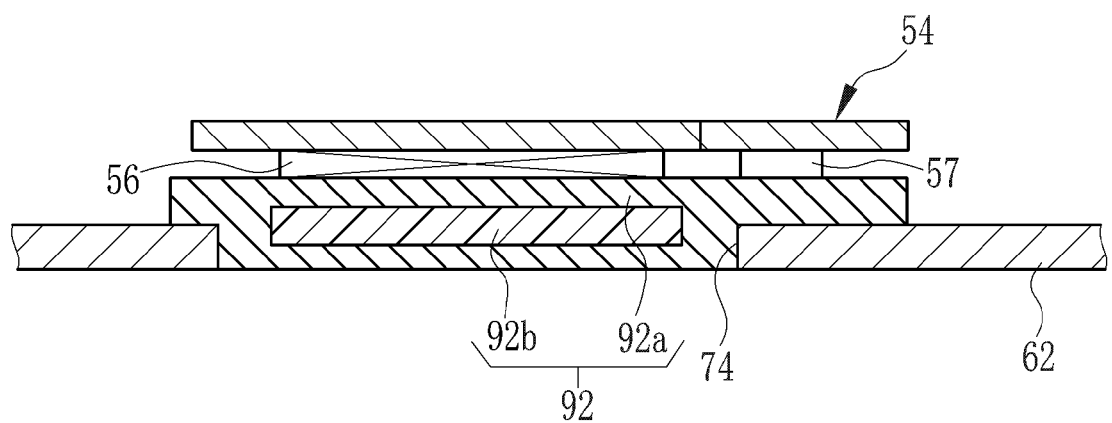
FIG. 8 is a cross section illustrating one preferred cover device having a core material.

In FIG. 8, another preferred cover device 92 includes a cover plate 92a and a core material 92b embedded in the cover plate 92a. A material of the cover plate 92a is elastomer such as silicone rubber. The core material 92b is formed from a plastic material similar to the cap 77. The core material 92b is a reinforcer for additional rigidity in a similar manner to the cap 77. A difference of the cover device 92 in FIG. 8 from the cover device 76 in FIG. 5 lies in a relationship between the reinforcer and an outer surface of the rear housing shell 62. In the cover device 92, the cover plate 92a of elastomer appears outside the rear housing shell 62. Also, the cover plate 92a can be preferably coated with resin for higher smoothness, so that a slipping property of the outer surface can be kept even in the use of the elastomer.

Figure 9:
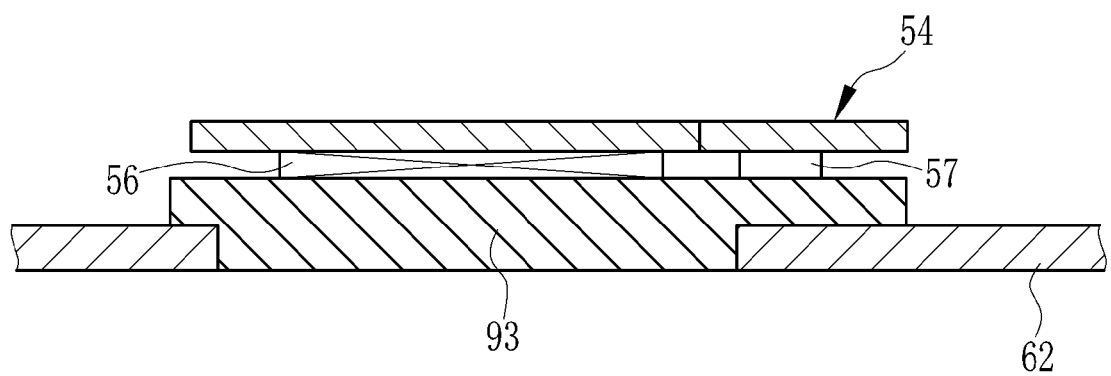
FIG. 9 is a cross section illustrating still another preferred cover device of a single piece.

In FIG. 9, still another preferred cover device 93 is formed from one material without a cap, core or other reinforcers of plastic material. An example of material for the cover device 93 is elastomer such as silicone rubber. The structure of the cover device 93 of the single material has a lower rigidity than those of FIGS. 5-8 because of insufficient reinforcement, but can be manufactured less costly than the structures of FIGS. 5-8 with the multiple parts. It is preferable to coat the surface of the cover device 93 with resin for smoothness in manner similar to that of the cover device 92 of FIG. 8.

The cover device 93 may be formed from a plastic material or synthetic resin other than elastomer. An acceptably drip-proof structure of the cover device 93 can be formed by the use of the plastic material. Also, a packing or sealing material can be additionally used with the cover device 93 of the plastic material for the purpose of a reliably drip-proof structure. Examples of the plastic material include thermoplastic resins and thermoset resins such as epoxy resin and phenolic resin. At first, the thermoset resin is in a softened state for assembling operation. After filling in the path opening 74, the thermoset resin is hardened for encapsulation, to obtain a drip-proof property of the cover device 93. No separate packing or sealing material is required in case the thermoset resin is used. Examples of the packing material are a rubber ring or band, or filler material of a thermoset resin or ultraviolet curable resin.

Figure 10:
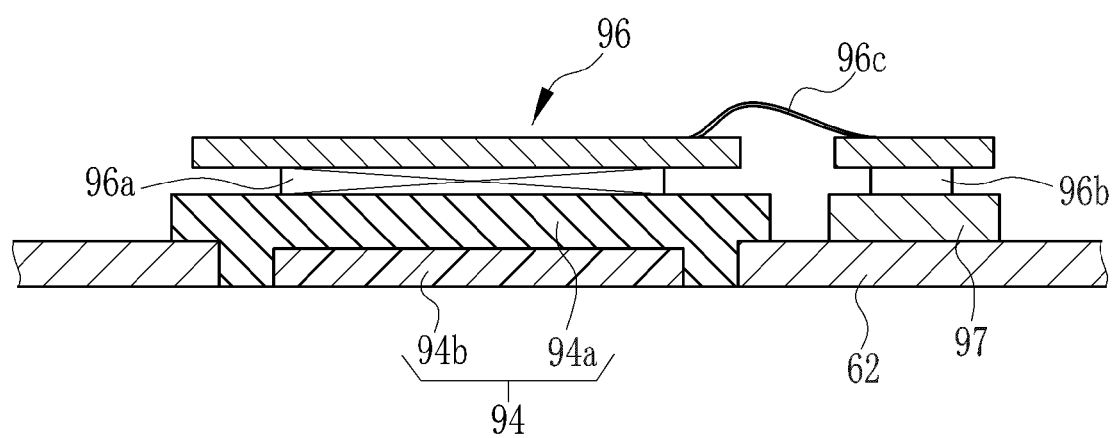
FIG. 10 is a cross section illustrating one preferred cover device contacting a power receiving coil.

In FIG. 10, a fourth preferred cover device 94 is illustrated, which is thermally coupled partially with a power receiver 96 or power receiving unit. The power receiver 96 includes a power receiving coil 96a or secondary inductive coil (energy receiver) and a circuit device 96b (power output device) mounted on substrates separate from one another. A wire line 96c electrically connects the power receiving coil 96a to the circuit device 96b. The cover device 94 extends entirely along the power receiving coil 96a. The cover device 94 contacts the power receiving coil 96a but does not contact the circuit device 96b. The cover device 94 is a heat dissipator of the power receiving coil 96a included in the power receiver 96. In the cover device 94, the cover device 76 of FIG. 5 is repeated but with a difference in having a cover plate 94a and a plastic cap 94b or cap plate (path plate). The cover plate 94a is formed from elastomer such as silicone rubber.

A heat dissipator 97 for the circuit device 96b is used typically with the cover device 94 which is thermally coupled only with the power receiving coil 96a of the power receiver 96. The heat dissipator 97 contacts the rear housing shell 62, and dissipates heat of the circuit device 96b to the rear housing shell 62 and the holder plate 82. The heat dissipator 97, although disposed outside a transmission path of the power E, should have an electrical insulating property for contact with the circuit device 96b. A preferable material for the heat dissipator 97 has the electrical insulating property and thermal conductivity similar to the cover device 94.

It is unnecessary in the heat dissipator 97 to consider a dust-proof structure or drip-proof structure, because the heat dissipator 97 does not close the path opening 74 in a manner of the cover device 94. A material for the heat dissipator 97 can be selected by considering the thermal conductivity. It is well-known that an amount of heat is higher at a circuit device than an electrode for power receiving in the structure of capacitive coupling type as a non-contact charging type. In the case of a high amount of heat of a circuit device, a combined structure of the cover device 94 and the heat dissipator 97 is preferable. The present example having the cover device 94 and the heat dissipator 97 is advantageous in that a size of the heat dissipator 97 added to the cover device 94 can be smaller than in an example in which the cover device 94 is not used for dissipating heat. Thus, the structure is effective in reducing a thickness and weight of the housing 32.

The cover device 94 is thermally coupled only with the power receiving coil 96a in the power receiver 96 in the embodiment, but can be coupled only with the circuit device 96b. See FIG. 10. There is no change in the position of the cover device 94 even for contact with only the circuit device 96b, as the cover device 94 should close the path opening 74. Instead of contact of the cover device 94 with the power receiving coil 96a, an extension arm is formed on the cover device 94 to extend to the circuit device 96b, and contacts the circuit device 96b. This example is advantageous in a high amount of heat of a circuit device without a problem of heating of a power receiving component (energy receiver) such as a coil and electrode.

In the above embodiments, the cover device contacts the power receiver 54 and the housing 32 directly for thermal conduction. However, a thermally conductive spacer may be disposed between a cover device and the power receiver 54 for indirectly combining each one of the power receiver 54 and the housing 32 with the cover device for thermal conduction. Although the cover device of FIGS. 5, 7 and 8 is constituted from the two components, a cover device can be constituted from three or more components attached together. Those components can be formed from the same material or from materials different from one another.

Figure 11:
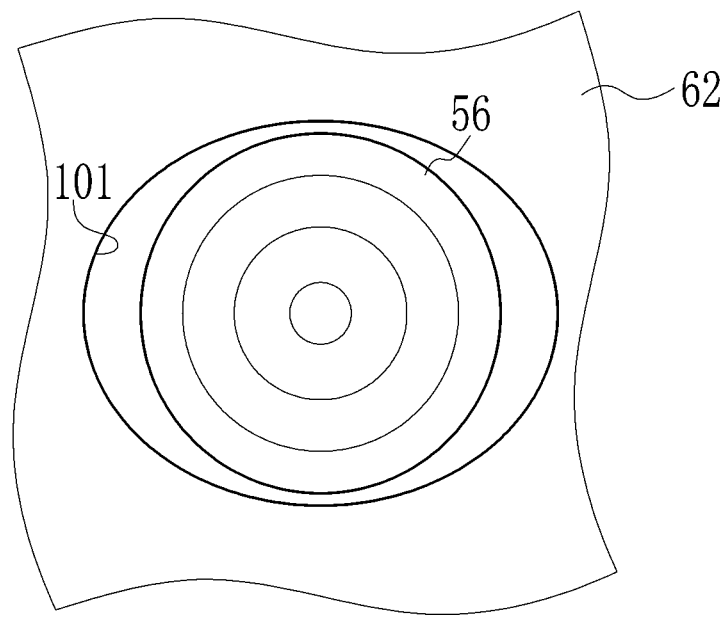
FIG. 11 is a plan illustrating another preferred opening in an elliptic shape.
Figure 12:
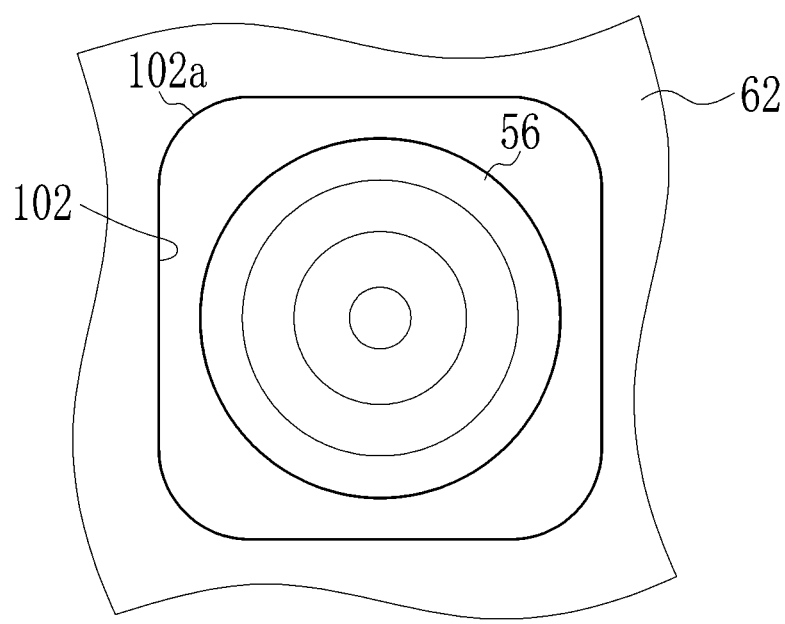
FIG. 12 is a plan illustrating one preferred opening in a quadrilateral shape with curved corners.

In the above embodiments, the path opening 74 is circular as illustrated in FIGS. 4 and 5. Furthermore, another preferred path opening 101 in FIG. 11 is elliptic. Also, an opening can be semicircular. In FIG. 12, still another preferred path opening 102 is quadrilateral. Also, an opening can be polygonal, for example, triangular or pentagonal. Note that it is preferable to define edges of the path opening at least partially with a curved line in consideration of rigidity of the rear housing shell 62. Of course, the circular or elliptic opening is entirely constituted by a curved line. In contrast with this, corners of an angular form are included in edges of the semicircular or polygonal opening. It is preferable to form a finely curved form at inner corners 102a of the path opening 102.

Figure 13:
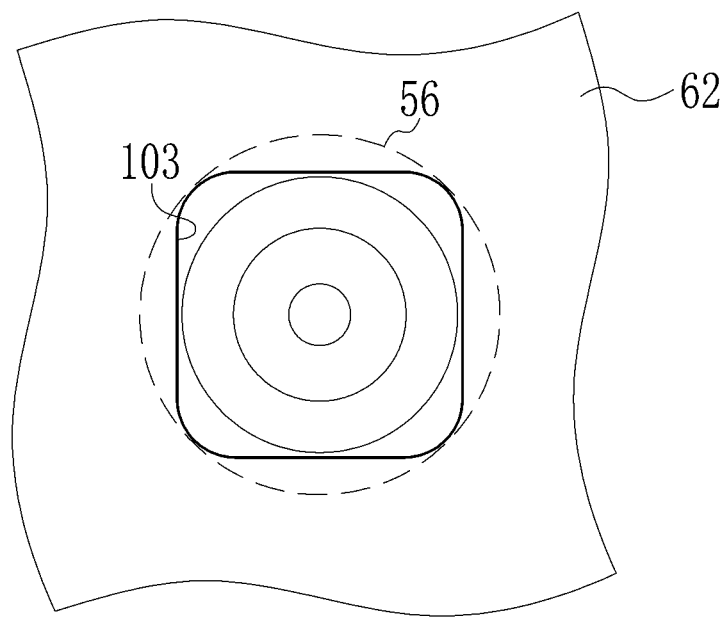
FIG. 13 is a plan illustrating still another preferred opening smaller than the power receiving coil.

In the above embodiments, the size of the path opening is as large as the power receiving coil 56 as illustrated in FIG. 5. In FIG. 13, an additional preferred path opening 103 is illustrated, and is smaller than the power receiving coil 56. As a transmission path for power extends through the path opening 103, the size of the path opening 103 can be preferably equal to or larger than the size of the power receiving coil 56 in view of minimizing electric loss. However, should the path opening 103 be too large, rigidity of the housing 32 will be too low. Accordingly, the size of the path opening 74 in FIG. 5 can be preferably equal to the size of the power receiving coil 56.

However, priority may be given to the rigidity of the housing 32 irrespective of a loss of a tolerable value. It is concluded that the path opening 103 of FIG. 13 is effectively smaller than the size of the power receiving coil 56. Furthermore, an area of the path opening 103 should be equal to or larger than a half of an area of the power receiving coil 56, because the electric loss should not be very high.

Also, it is preferable that an upper limit of the area of the path opening is two times as large as the area of the power receiving coil 56 so as to keep the rigidity of the housing 32 without remarkable drop. In short, a preferable range of the area S1 of the path opening is expressed by the condition $(1/2) \cdot S2 \le S1 \le 2 \cdot S2$ where S2 is the area of the power receiving coil 56. It is further preferable that the area S1 of the path opening is substantially equal to the area S2 of the power receiving coil 56 in consideration of balancing the effects of reducing the loss in the power and keeping the rigidity of the housing 32. Note that the conception of the substantial equality includes the exact equality and the approximate equality in which a difference between those is at most ±10%.

The magnetic flux density of the power receiving coil 56 is higher at its center than at its peripheral positions. The portion with the high magnetic flux density should be preferably aligned with the path opening. In the case of the path opening 103 with a smaller area than that of the power receiving coil 56, the path opening 103 can be preferably disposed concentrically with the power receiving coil 56. Thus, it is possible to keep high efficiency in power reception. Note that the path opening 103 can be at least positioned centrally of the power receiving coil 56 without the correctly concentric form. In short, the center of the power receiving coil 56 can be included in a portion of the path opening 103 aligned with the power receiving coil 56.

Figure 14:
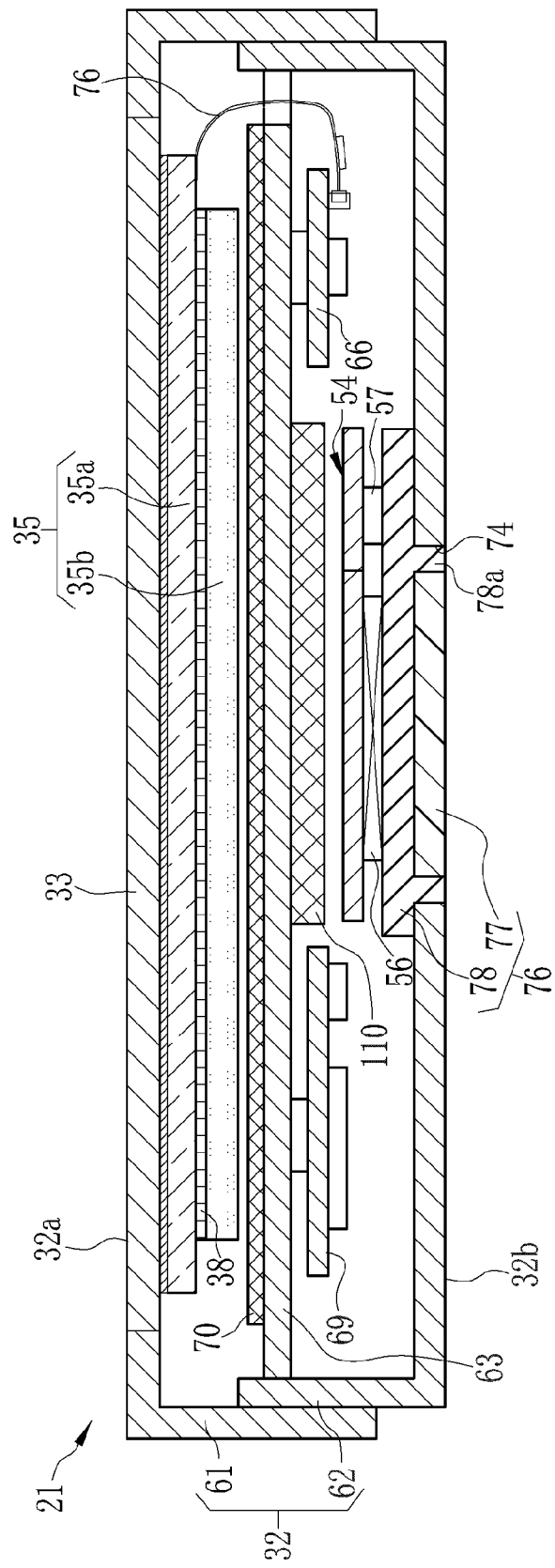
FIG. 14 is a cross section illustrating another preferred embodiment with a thermal insulator.

In FIG. 14, a preferred embodiment is illustrated in which a thermal insulator 110 is disposed between the power receiver 54 and the support plate 63. As the thermal insulator 70 of FIG. 5 is repeated, the thermal insulator 110 is formed from a sponge sheet or porous sheet. The thermal insulator 110 shields heat of the power receiver 54 from the active pixel area 38 of the detection panel 35. This is effective in preventing the temperature of the active pixel area 38 from increasing locally due to the heat of the power receiver 54. In FIG. 14, the power receiver 54 is attached to the rear housing shell 62 with the cover device 76 unlike the form in FIG. 5. However, the power receiver 54 can be attached to the support plate 63 with the thermal insulator 110.

Also, an interval between the power receiver 54 and the detection panel 35 can be preferably set larger than an interval between the detection panel 35 and the circuit boards 66-69 to keep an insulating space in place of using the thermal insulator 110. In short, air is used for thermal insulation. The insulating space is less effective than the thermal insulator 110, but still more effective than a structure of a direct contact without an insulating space.

The above embodiments are a battery built-in type in which the housing 32 does not have an opening for removing the rechargeable battery 53. However, an opening may be formed in the housing 32 for mounting the battery 53 in a removable manner. For the removable structure, a charging method can be not only the non-contact charging method but a contact charging method. In the non-contact charging method, the battery 53 is charged by the wireless power transmission apparatus 81 while mounted on the housing 32. In the contact charging method, the battery 53 is separated from the housing 32, set on a charger of a contact type, and charged.

In the above embodiments, the electronic cassette is capable of wireless communication and has the radiation imaging detector 31 powered with a battery. Also, the electronic cassette can have an interface for wired communication. The electronic cassette can include a selector for selecting one of the wireless communication and the wired communication for use in the imaging. Furthermore, a power supply of a commercial power source with a power supply cable can be used to power the radiation imaging detector 31 in addition to powering of the battery. A selector can be operated for selecting one of the commercial power source and the battery for use. The power from the commercial power source is used for charging the battery and powering the radiation imaging detector 31.

In FIG. 15, a variant of the holder plate 82 of the wireless power transmission apparatus 81 is illustrated for increasing the heat dissipation of the power receiver 54. A good thermal conductor 120 is included in the holder plate 82 and disposed around the path window 83 (path wall) with higher thermal conductivity than a remaining portion. The good thermal conductor 120 extends from the holder plate 82 toward an end of the housing. A cover device is directed to the good thermal conductor 120 as a heat dissipator of the power receiver 54. Heat can be dissipated by the good thermal conductor 120 after conduction in the cover device and the housing 32. Thus, effect of the heat dissipation can be ensured. As the good thermal conductor 120 is not disposed in a path portion for transmitting the power E, the good thermal conductor 120 does not require an electrical insulating property. Also, the good thermal conductor 120 can be formed from heat insulating material, and also the path window 83 (path wall) can be a good thermal conductor.

In the above embodiment, the power receiver 54 in the electronic cassette 21 is disposed substantially at the center of its rear surface 32b. However, the power receiver 54 can be disposed at any point in the rear surface 32b, for example, near to an edge or corner. Also, the power receiver 54 may be disposed on a lateral surface of the electronic cassette 21.

Also, various known techniques can be used in the preferred embodiments of the invention in relation to a size and characteristics of the power transmission coil and power receiving coil, arrangement of and an interval between the wireless power transmission apparatus and power receiver in the wireless power supply system, and the like.

The present invention is not limited to the above-described embodiments. Features of the embodiments and variants may be combined with one another. Radiation in the electronic cassette for the radiographic imaging is X-rays in the embodiments above, but can be gamma rays or the like.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic cassette for radiographic imaging comprising:
    a radiation imaging detector for detecting a radiation image of an object according to radiation from said object;
    a battery for supplying said radiation imaging detector with power;
    a power receiver for wirelessly receiving power from a wireless power transmission apparatus for charging said battery;
    a housing, formed from an electrical conductor, for containing said radiation imaging detector and said power receiver;
    a path opening, formed in said housing, and disposed in alignment with said power receiver;
    a cover device, formed from a material having electrical insulating property and thermal conductivity, for closing said path opening, and conducting heat of said power receiver to said housing for dissipation, said cover device including:
        a cap plate for opposing to said wireless power transmission apparatus;
        a cover plate, disposed between said cap plate and said power receiver, and having a higher thermal conductivity than a thermal conductivity of said cap plate;
    a projection, formed to project from said cover plate along an edge of said cap plate, for directing heat of said power receiver outwards.

2. An electronic cassette as defined in claim 1, wherein said cover device includes:
    a first portion; and
    a second portion, attached to said first portion, and formed from a material different from a material of said first portion.

3. An electronic cassette as defined in claim 1, wherein said cover device contains synthetic resin.

4. An electronic cassette as defined in claim 3, wherein said synthetic resin contains elastomer.

5. An electronic cassette as defined in claim 4, wherein said elastomer is silicone rubber.

6. An electronic cassette as defined in claim 3, wherein said cover device contains elastomer and a plastic material.

7. An electronic cassette as defined in claim 1, wherein said power receiver includes:
    an energy receiver for receiving electromagnetic energy from said wireless power transmission apparatus and generating said power;
    a circuit device for supplying said battery with said power from said energy receiver;
    said path opening is aligned with said energy receiver and positioned centrally of said energy receiver.

8. An electronic cassette as defined in claim 7, wherein an area of said path opening is equal to or larger than a half of an area of said energy receiver.

9. An electronic cassette as defined in claim 7, wherein an area of said path opening is equal to or smaller than two times an area of said energy receiver.

10. An electronic cassette as defined in claim 7, wherein an area of said path opening is substantially equal to an area of said energy receiver.

11. An electronic cassette as defined in claim 7, wherein a profile line of said path opening is at least partially curved.

12. An electronic cassette as defined in claim 7, wherein said path opening is circular.

13. An electronic cassette as defined in claim 7, wherein said path opening includes:
    at least one inner corner; and
    a curved portion for curving an edge of said inner corner.

14. An electronic cassette as defined in claim 7, wherein said cover device is thermally coupled with at least one of said energy receiver and said circuit device.

15. An electronic cassette as defined in claim 7, wherein said
    cover plate is disposed between said cap plate and said energy receiver, and
    said projection directs heat of said energy receiver outwards.

16. An electronic cassette as defined in claim 1, further comprising a thermal insulator disposed between said power receiver and said radiation imaging detector in said housing.

17. An electronic cassette as defined in claim 16, wherein said thermal insulator is a space.

18. An electronic cassette as defined in claim 1, wherein said electrical conductor contains at least one of carbon graphite and metal.

* * * * *